(12) United States Patent
Singhala et al.

(10) Patent No.: US 10,952,754 B2
(45) Date of Patent: Mar. 23, 2021

(54) ORTHOPEDIC SURGICAL GUIDE FOR TUNNEL PLACEMENT

(71) Applicant: THE JOHNS HOPKINS UNIVERSITY, Baltimore, MD (US)

(72) Inventors: Mohit Singhala, Baltimore, MD (US); Matthew Lerner, Baltimore, MD (US); Polly Charlene Ma, Freemont, CA (US); Andrew Jann, Diamond Bar, CA (US); Rachel An, Buffalo Grove, IL (US); Bashir Ahmed Zikria, Bethesda, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/973,807

(22) Filed: May 8, 2018

(65) Prior Publication Data

US 2018/0317941 A1 Nov. 8, 2018

Related U.S. Application Data

(60) Provisional application No. 62/502,907, filed on May 8, 2017.

(51) Int. Cl.
*A61B 17/17* (2006.01)
*A61B 17/16* (2006.01)
*A61B 1/317* (2006.01)

(52) U.S. Cl.
CPC ...... *A61B 17/1764* (2013.01); *A61B 17/1633* (2013.01); *A61B 17/1714* (2013.01); *A61B 1/317* (2013.01)

(58) Field of Classification Search
CPC . A61B 17/17; A61B 17/1764; A61B 17/1714; A61B 17/1716; A61B 17/16; A61B 17/1633; A61B 1/317
See application file for complete search history.

(56) References Cited

U.S. PATENT DOCUMENTS

| | | | |
|---|---|---|---|
| 4,672,957 A | 6/1987 | Hourahane | |
| 4,722,331 A | 2/1988 | Fox | |
| 5,350,383 A | 9/1994 | Schmieding et al. | |
| 5,562,664 A | 10/1996 | Durlacher et al. | |
| 6,342,056 B1 | 1/2002 | Mac-Thiong et al. | |
| 8,292,894 B2 | 10/2012 | He | |
| 8,317,862 B2 | 11/2012 | Troger et al. | |
| 8,323,291 B2 | 12/2012 | Dienst et al. | |
| 8,491,595 B2 | 7/2013 | Volpi et al. | |
| 8,617,176 B2 | 12/2013 | Lizardi et al. | |
| 8,986,314 B1 * | 3/2015 | Jordan | A61B 17/1714 606/96 |
| 2011/0125159 A1 * | 5/2011 | Hanson | A61B 17/1764 606/96 |

* cited by examiner

*Primary Examiner* — Christopher J Beccia
(74) *Attorney, Agent, or Firm* — Johns Hopkins Technology Ventures (57) ABSTRACT

The present invention provides a drill guide for orthopedic surgery. The drill guide is configured to facilitate drilling of a bone tunnel with a correct and repeatable placement. The drill guide is designed for drilling of the femoral bone during knee surgery. More particularly, in certain embodiments the drill guide is designed for ACL repair and replacement surgery. In a preferred embodiment of the present invention, the guide has 5 members: a center rail, a side rail, an anteromedial slider, a femoral slider, and a center pin.

21 Claims, 7 Drawing Sheets

ORTHOPEDIC SURGICAL GUIDE FOR TUNNEL PLACEMENT

CROSS REFERENCE TO RELATED APPLICATIONS

This application claims the benefit of U.S. Provisional Patent Application No. 62/502,907 filed on May 8, 2017, which is incorporated by reference, herein, in its entirety.

FIELD OF INVENTION

The present invention relates generally to the field of medical devices. More particularly, the present invention relates to an orthopedic surgical guide for tunnel placement.

BACKGROUND

During arthroscopic knee procedures, particularly anterior cruciate ligament (ACL) reconstruction, the torn ligament is removed so the surgeon can see the original ligament attachment sites on the bone, known as the footprints. Tunnels are drilled into the femur and tibia through the footprints to make anchor points for a graft. The graft is then passed through the tunnels and fixed in place. The placement of the tunnels is critical for a successful surgery. Drilling the tunnels through the footprints contributes to an anatomical placement, but of the two tunnels, the femoral tunnel in particular is more difficult to place accurately. With current techniques and tools for ACL tunnel placements, it is difficult for surgeons to create, in a reproducible way, anatomical femoral tunnel placements. It is desirable to provide a drill guide, which allows for more accurate femoral tunnel placement.

A method and device for accurate and reproducible placement of tunnels into the bone are therefore needed.

SUMMARY

The foregoing needs are met, to a great extent, by the present invention wherein in one aspect, a drill-guide device for orthopedic surgery includes a center rail having two isocentric rails and a port. The device includes a side rail. The side rail is configured to slidably couple to a first of the two isocentric rails of the center rail. The device also includes an anteromedial slider and a femoral slider. The anteromedial slider is slidably coupled to the side rail, and the femoral slider is slidably coupled to a second of the two isocentric rails.

According to an embodiment of the present invention, the device includes a center pin. The center pin is configured to be removably disposed through the port of the center rail. A size and a shape of the center pin can be adjusted according to the anatomical structure and the type of tunnel being drilled. The center pin is configured to target the position where drilling should take place.

According to another embodiment of the present invention, the center rail forms a section of a sphere with both arcs cut out at the same radius. A shape of the center rail is configured such that any tool entering normal to a surface of the center rail always points towards a center of the sphere. The center rail is configured to enable placement of a physical or virtual target at a desired spot (center of the sphere). The port of the center rail is configured to receive an arthroscope. The first of the isocentric rails of the center rail extends from a center point of the center rail in a longitudinal direction. The second of the isocentric rails of the center rail extends from a center point of the center rail in a latitudinal direction. The device is further configured for direct arthroscopic visualization of a femoral footprint through the anteromedial port at 90° flexion. The device is configured for knee surgery.

According to yet another embodiment of the present invention, the anteromedial slider comprises a port. The port of the anteromedial slider is configured for placement and removal of tools including drill bits and bone taps. The femoral slider also comprises a port. The port of the femoral slider is configured for placement and removal of tools including drill bits and bone taps. The anteromedial slider and the femoral slider are configured to place tools through different parts of the knee anatomy. The device of claim 1 wherein the femoral slider and the center pin are positioned around a femoral footprint on the center rail. The anteromedial slider slides in a y-z-plane. The femoral slider slides in an x-y-plane. The device is configured to allow maintenance of a record at which each of its components were placed during surgery. The device can be used as a patient-specific guide in revision surgery by allowing user to create the arrangement in which the components were placed for the first surgery. The device parameters can be adjusted based on subject/patient anatomy. The device can include marking on at least one selected from a group consisting of: the side rail, the center rail, the anteromedial slider, and the femoral slider.

BRIEF DESCRIPTION OF THE DRAWINGS

Further objectives and advantages will become apparent from a consideration of the description, drawings, and examples.

DETAILED DESCRIPTION

The presently disclosed subject matter will now be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention provides a drill guide for orthopedic surgery. The drill guide is configured to facilitate drilling of a bone tunnel with a correct and repeatable placement. The drill guide is designed for drilling of the femoral bone during knee surgery. More particularly, in certain embodiments the drill guide is designed for ACL repair and replacement surgery. In a preferred embodiment of the present invention, the guide has 5 members: a center rail, a side rail, an anteromedial slider, a femoral slider, and a center pin.

Figure 1:
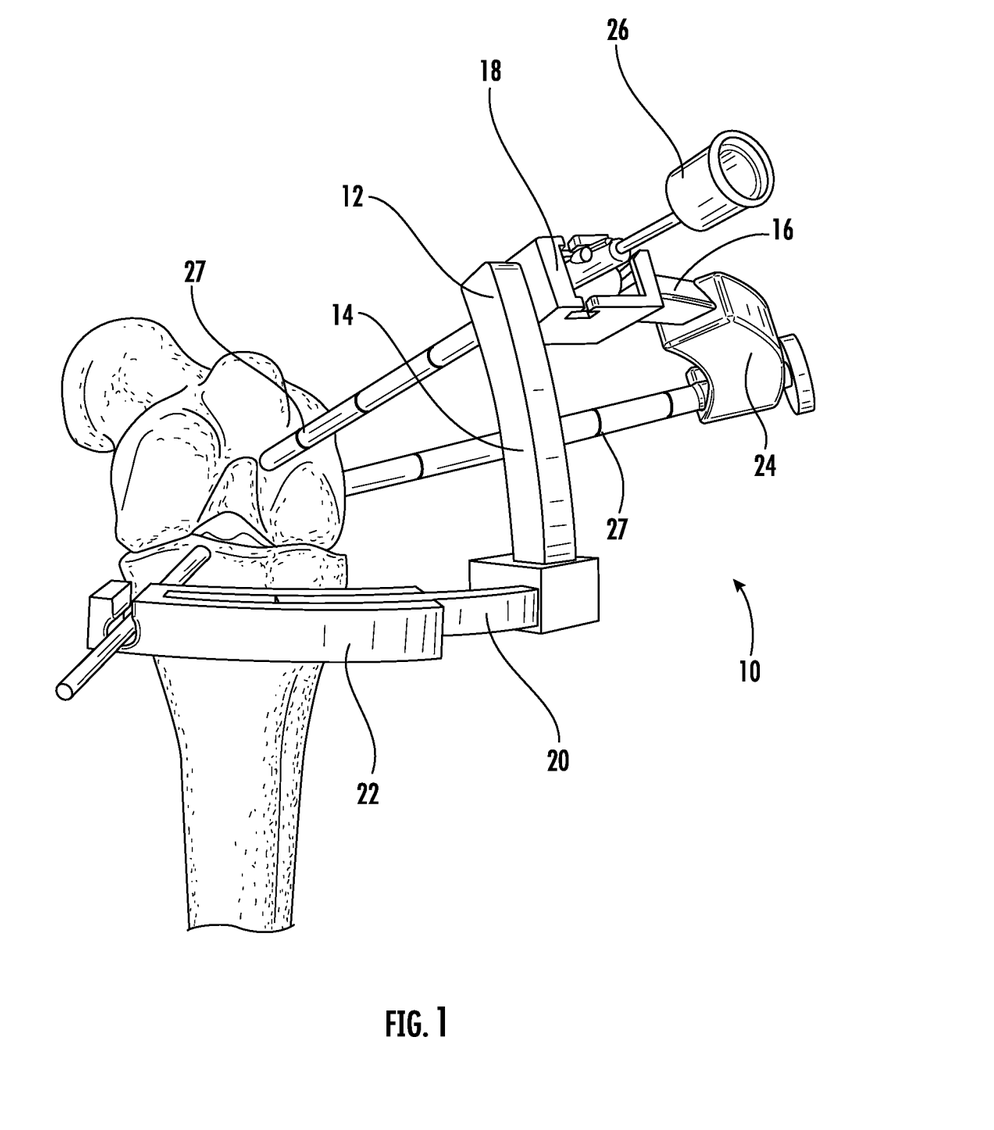
FIG. 1 illustrates a perspective view of a drill guide positioned on a knee joint, according to an embodiment of the present invention.
Figure 2:
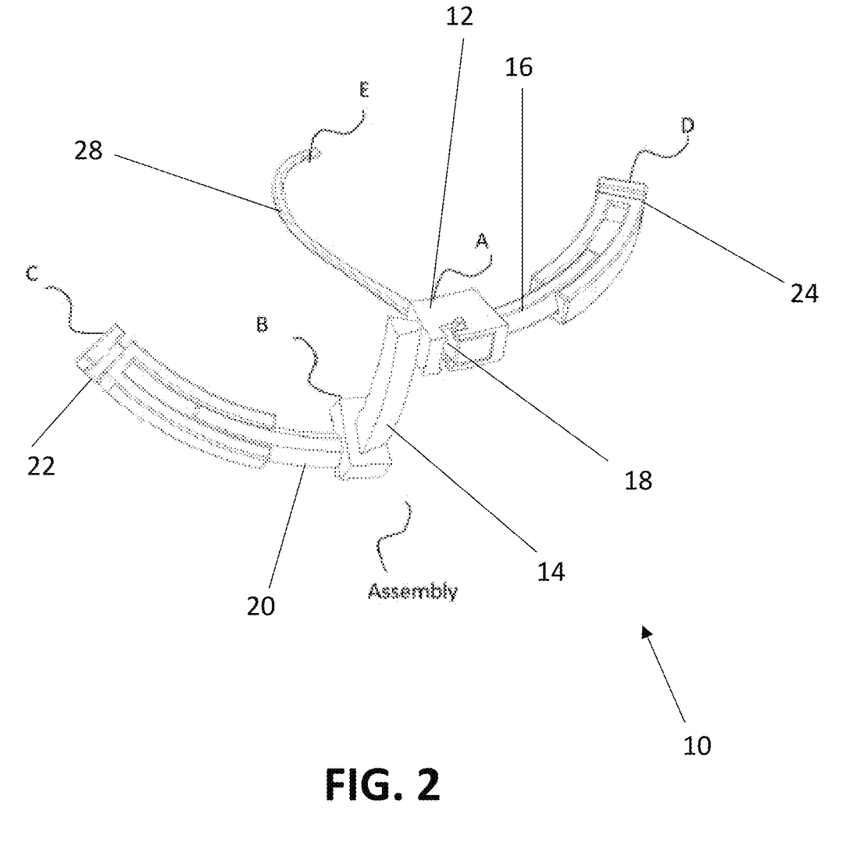
FIG. 2 illustrates a perspective view of a drill guide, according to an embodiment of the present invention.

FIG. 1 illustrates a perspective view of a drill guide positioned on a knee joint, and FIG. 2 illustrates a perspective view of an assembled drill guide, both according to an embodiment of the present invention. As illustrated in FIGS. 1 and 2, the drill guide 10 includes a center rail 12. The center rail 12 is the hub of the drill guide device 10. The center rail 12 includes two isocentric rails 14, 16, and a port 18. The two isocentric rails 14, 16 have a generally arced shape. Isocentric rail 14 extends from the center in a longitudinal direction and isocentric rail 16 extends from the center in a latitudinal direction. A side rail 20 is slidably coupled to the isocentric rail 14 that extends in the longitudinal direction. An anteromedial slider 22 is slidably coupled to the side rail 20, and a femoral slider 24 is slidably coupled to the isocentric rail 16 that extends in the latitudinal direction. FIG. 1 illustrates a drill guide 26 disposed through the port 18 of the center rail 12. The drill guide 26 can include markings 27 to assist in visualizing and recording the angle and position at which the guide was used in respect to other components during its operation.

FIG. 2 illustrates a center pin 28 is positioned in the port 18 of center rail 12 and helps in targeting the spot at which drilling needs to take place. The size and shape of the center pin can be adjusted according to the anatomical structure and the type of tunnel being drilled (i.e. tibial, femoral, etc). It should be noted that the size of the overall device can vary based on the patient and the procedure. It is also possible that the device can be custom made and sized based on information about the patient, such as information from a CT scan, X-Ray, or MRI.

With respect to FIG. 1, the femoral slider 24 and the center pin 28 are positioned around the femoral footprint on the center rail 12. The center pin 28 is inserted through the port 18 of the center rail. Direct arthroscopic visualization of the femoral footprint can be achieved through the anteromedial port 18 at 90 degree flexion. A cannulated drill sleeve is tapped to fix the femoral slider 24 on the femur through a lateral femoral incision. The center pin 28 is removed and the arthroscope is moved to the anterolateral port 18. For drilling, the anteromedial slider 22 and the side rail are coupled to the center rail 12. A guide pin is drilled through the anteromedial port 18 into the femoral footprint, followed by standard drilling and graft fixation techniques. The configuration of the device is three-dimensional and based on a spherical shape. This allows for isocentricity in three dimensions.

Figure 3A:
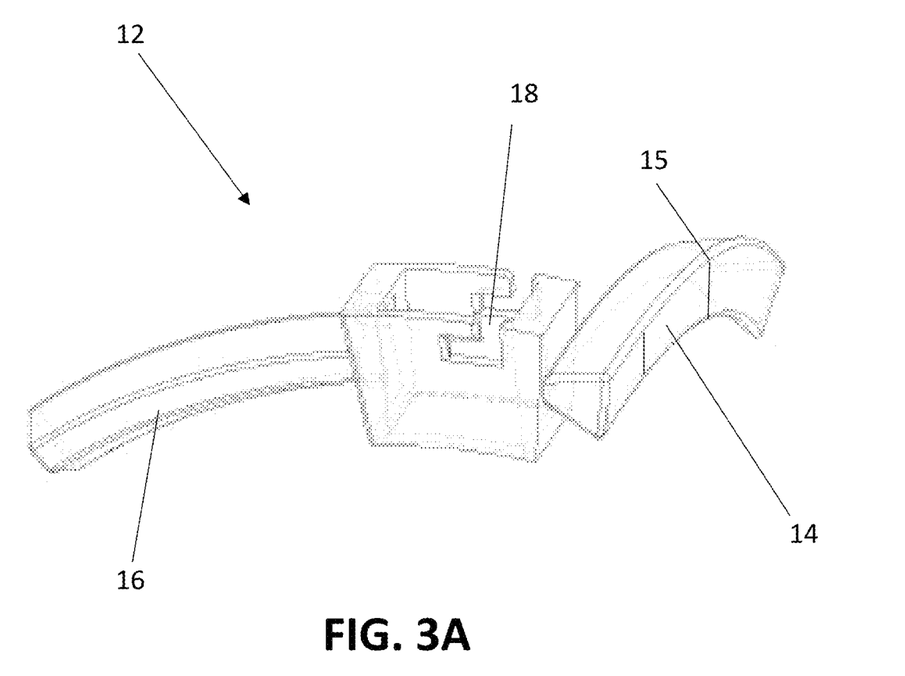
FIG. 3A illustrates a perspective view of a side rail of the drill guide, according to an embodiment of the present invention.

FIG. 3A illustrates a perspective view of a center rail of the drill guide, according to an embodiment of the present invention. The center rail 12 is the hub of the device assembly with two isocentric rails 14, 16 and a port 18. In some embodiments, the center rail 12 forms a section of a sphere with both the arcs cut out at the same radius. The shape of the center rail 12 ensures that any tool entering normal to the surface of the center rail, always points towards a center of the sphere. The design of the present invention therefore enables placement of a physical or virtual target at a desired spot (center of the sphere). The isocentric rail 14 can include markings 15 for reference and repeatable placement of the side rail 20 along the isocentric rail 14. The markings 15 assist in visualizing and recording the angle at which the rail was used in respect to other components during its operation.

Figure 3B:
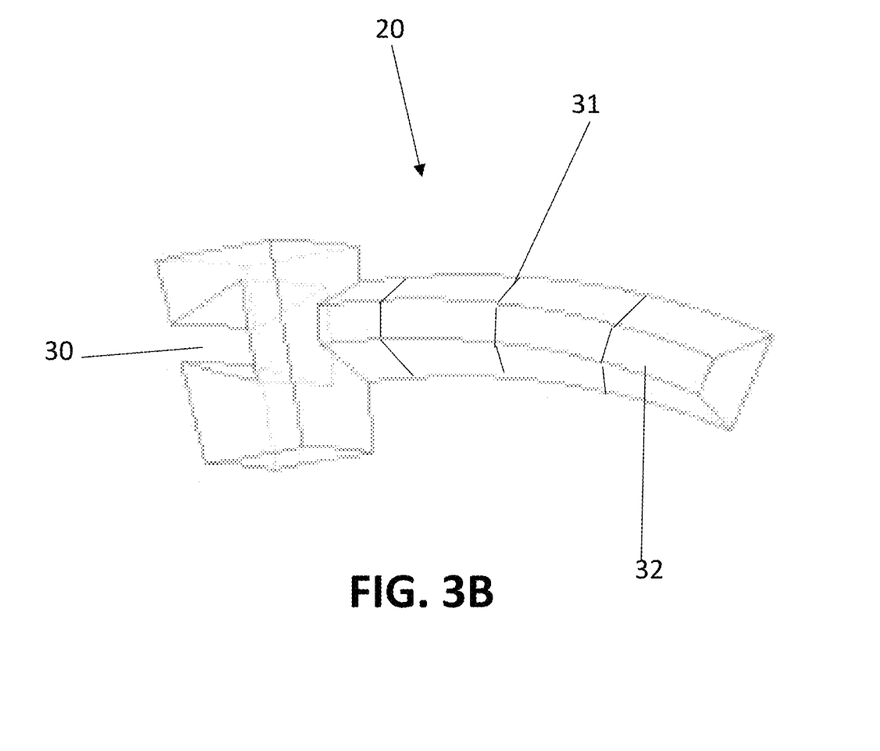
FIG. 3B illustrates a perspective view of a side rail of the drill guide, according to an embodiment of the present invention.

FIG. 3B illustrates a perspective view of a side rail of the drill guide, according to an embodiment of the present invention. The side rail 20 is an extension that allows for movement along the isometric rail of the center rail that extends in a longitudinal direction. Coupling 30 slides on the isocentric rail of the center rail that extends longitudinally. The side rail accommodates the anteromedial slider on arm 32. This configuration enables motion in the YZ plane for the anteromedial slider. The side rail may have markings 31 that assist in visualizing and recording the angle at which the rail was used in respect to other components during its operation.

Figure 3C:
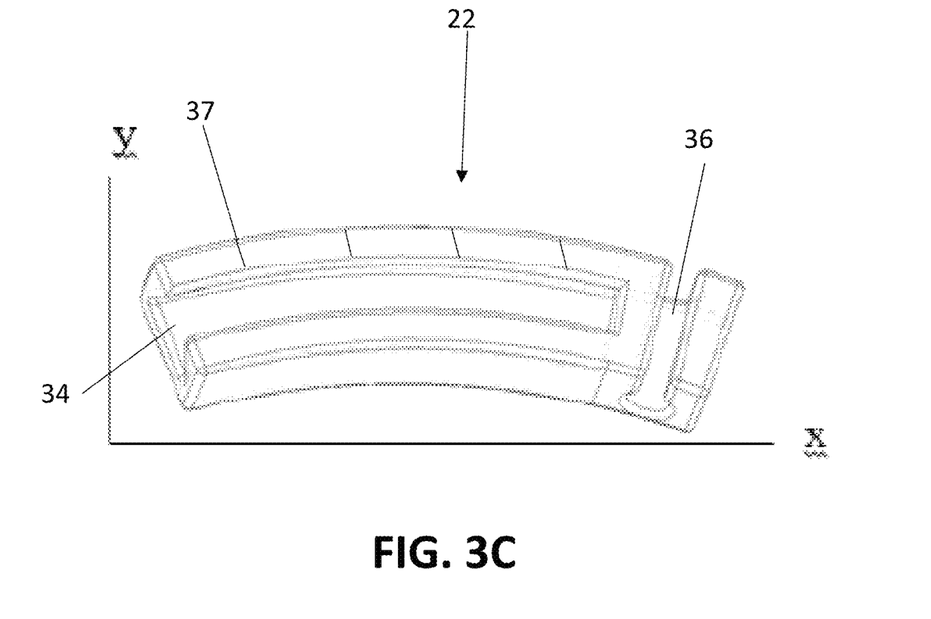
FIG. 3C illustrates a perspective view of an anteromedial slider of the drill guide, according to an embodiment of the present invention.

FIG. 3C illustrates a perspective view of an anteromedial slider of the drill guide, according to an embodiment of the present invention. The anteromedial slider 22 acts as a handle that defines a slot 34 designed to complement the shape of the extensions on the side rail. The anteromedial slider 22 also defines a through hole 36, which allows for placement and removal of tools like drill bits, bone taps etc. The complementary shape of the slot 34 allows for the anteromedial slider 22 to slide along the arc established earlier with the center and side rails. The anteromedial slider 22 also acts as a part of the same sphere once attached to the assembly). The anteromedial slider 22 also moves in XY plane with respect to its own base. The anteromedial slider 22 can also include markings 37 for reference and repeatable placement of the slider. The markings 37 assist in visualizing and recording the angle at which the slider was used in respect to other components during its operation.

Figure 3D:
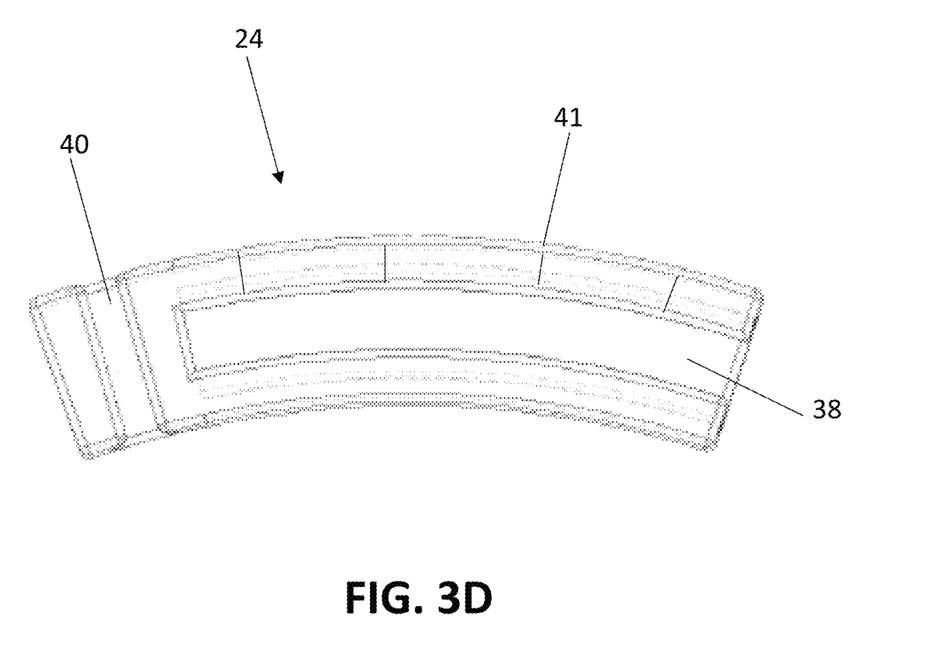
FIG. 3D illustrates a top down view of a femoral slider of the drill guide, according to an embodiment of the present invention.

FIG. 3D illustrates a top down view of a femoral slider of the drill guide, according to an embodiment of the present invention. The femoral slider 24 is similar in shape and design to the anteromedial slider, but the femoral slider 24 also mirrors the side face of the handle (smaller rectangular cross-section). The femoral slider 24 attaches directly to the center rail and slides on the XY plane. Both the anteromedial and femoral sliders are used to place tools through different parts of the knee anatomy. The femoral slider 24 acts as a handle that defines a slot 38 designed to complement the shape of the extensions on the side rail. The femoral slider 24 also defines a through hole 40, which allows for placement and removal of tools like drill bits, bone taps etc. The complementary shape of the slot 38 allows for the femoral slider 24 to slide along the arc established earlier with the center and side rails. The femoral slider 24 can also include markings 41 for reference and repeatable placement of the slider. The markings 41 assist in visualizing and recording the angle at which the slider was used in respect to other components during its operation.

Figure 3E:
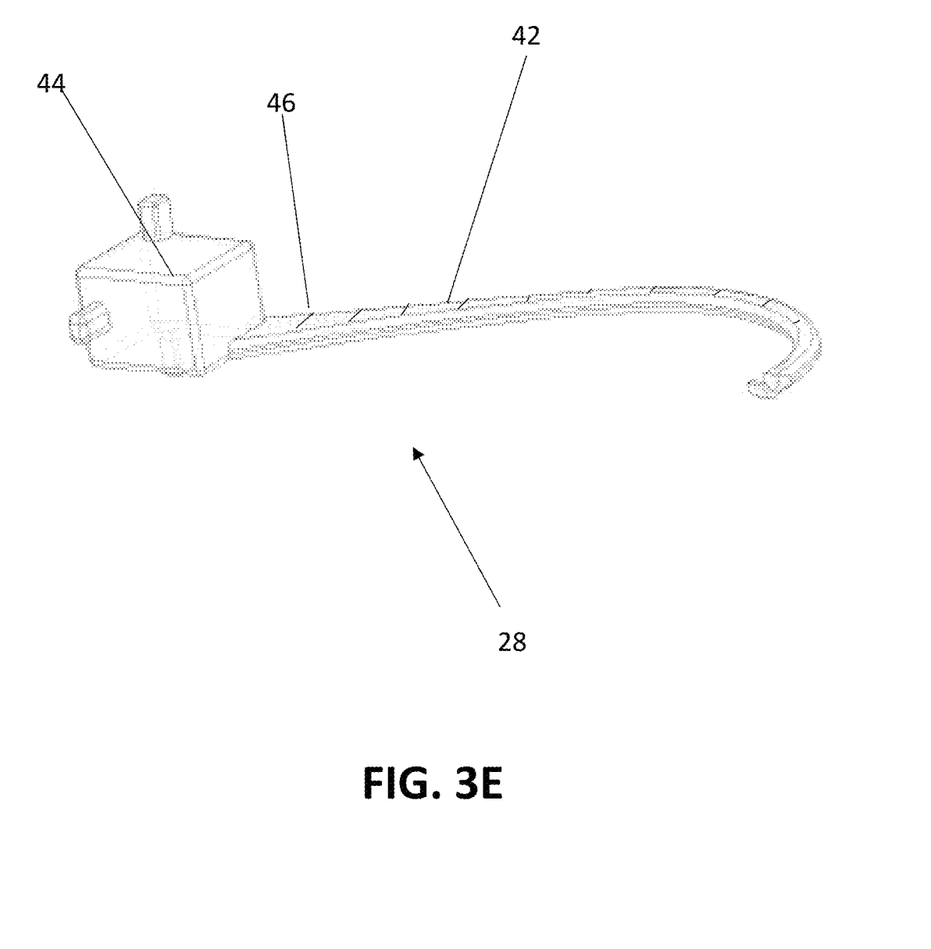
FIG. 3E illustrates a perspective view of a center pin of the drill guide, according to an embodiment of the present invention.

FIG. 3E illustrates a perspective view of a center pin of the drill guide, according to an embodiment of the present invention. The center pin 28 is removably insertable into the port cavity of center rail and helps in targeting the spot at which drilling needs to take place. The size and shape of the center pin 28 can also be adjusted according to the anatomical structure and the type of tunnel being drilled (i.e. tibial, femoral, etc.). The center pin 28 includes an elongate member 42 and a hub 42. The elongate member 42 can include markings 46 for reference and repeatable placement of the pin. The markings 46 allow for the user to visualize and record the distance for which the pin was inserted.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A drill-guide device for orthopedic surgery comprising:
a center rail having two isocentric rails and a center port;
a side rail, wherein the side rail is configured to slidably couple to a first of the two isocentric rails of the center rail;
an anteromedial slider, wherein the anteromedial slider is slidably coupled to the side rail and the side rail comprises an anteromedial port;
a femoral slider, wherein the femoral slider is slidably coupled to a second of the two isocentric rails and the femoral slider comprises a femoral port;
a center pin, wherein the center pin is configured to be removably disposed through the port of the center rail; and,
wherein the center rail, side rail, anteromedial slider, and femoral slider are arranged three-dimensionally, such that the drill-guide provides isocentricity in three-dimensions.

2. The device of claim 1 wherein a size and a shape of the center pin can be adjusted according to the anatomical structure and the type of tunnel being drilled.

3. The device of claim 1 wherein the center rail forms a section of a sphere with both arcs cut out at the same radius.

4. The device of claim 1 wherein a shape of the center rail is configured such that any tool entering normal to a surface of the center rail always points towards a center of the sphere.

5. The device of claim 1 wherein the center rail is configured to enable placement of a physical or virtual target at a desired spot (center of the sphere).

6. The device of claim 1 wherein the port of the anteromedial slider is configured for placement and removal of tools including drill bits and bone taps.

7. The device of claim 1 wherein the port of the femoral slider is configured for placement and removal of tools including drill bits and bone taps.

8. The device of claim 1 wherein the port of the center rail is configured to receive an arthroscope.

9. The device of claim 1 wherein the anteromedial slider and the femoral slider are configured to place tools through different parts of the knee anatomy.

10. The device of claim 1 wherein the first of the isocentric rails of the center rail extends from a center point of the center rail in a longitudinal direction.

11. The device of claim 1 wherein the second of the isocentric rails of the center rail extends from a center point of the center rail in a latitudinal direction.

12. The device of claim 1 further configured for direct arthroscopic visualization of a femoral footprint through the anteromedial port at 90° flexion.

13. The device of claim 1 wherein the femoral slider and the center pin are positioned around a femoral footprint on the center rail.

14. The device of claim 1 wherein the anteromedial slider slides in a y-z-plane.

15. The device of claim 1 wherein the femoral slider slides in an x-y-plane.

16. The device of claim 1 wherein the center pin is configured to target the position where drilling should take place.

17. The device of claim 1 wherein the device is configured for knee surgery.

18. The device of claim 1 wherein the device is configured to allow maintenance of a record at which each of its components were placed during surgery.

19. The device of claim 1 wherein the device can be used as a patient-specific guide in revision surgery by allowing user to create the arrangement in which the components were placed for the first surgery.

20. The device of claim 1 wherein the device parameters can be adjusted based on subject/patient anatomy.

21. The device of claim 1 further comprising marking on at least one selected from a group consisting of: the side rail, the center rail, the anteromedial slider, and the femoral slider.

* * * * *